US007878197B2

(12) United States Patent
Christy et al.

(10) Patent No.: US 7,878,197 B2
(45) Date of Patent: Feb. 1, 2011

(54) NASAL COMFORT DEVICES AND METHODS

(75) Inventors: Frank L. Christy, 117 Springline Dr., Vero Beach, FL (US) 32963; Stephen C. Keiser, Vienna, WV (US); Richard L. Miller, Needham, MA (US); Benjamin Powers, Boston, MA (US); Peter H. Swai, Weymouth, MA (US)

(73) Assignee: Frank L. Christy, Vero Beach, FL (US)

( * ) Notice: Subject to any disclaimer, the term of this patent is extended or adjusted under 35 U.S.C. 154(b) by 1028 days.

(21) Appl. No.: 11/704,684

(22) Filed: Feb. 9, 2007

(65) Prior Publication Data

US 2007/0221219 A1 Sep. 27, 2007

Related U.S. Application Data

(60) Provisional application No. 60/771,800, filed on Feb. 9, 2006.

(51) Int. Cl.
*A61M 15/00* (2006.01)
*A61M 15/08* (2006.01)

(52) U.S. Cl. .................. 128/204.13; 128/204.12; 128/203.12; 128/203.21; 128/203.19

(58) Field of Classification Search ........... 128/200.24, 128/200.28, 203.12–203.16, 203.19–203.23, 128/204.11–204.14, 205.27–206.15, 206.17–206.21, 128/206.25–206.26, 207.13; 424/402, 411, 424/422, 443, 447; 514/957–959, 965; 239/36–43, 239/53–56; 422/123–124, 305–306; 222/187; 141/110–111
See application file for complete search history.

(56) References Cited

U.S. PATENT DOCUMENTS

| 888,869 | A | 5/1908 | Clark |
| 3,993,072 | A | 11/1976 | Zaffaroni |
| 4,151,616 | A | 5/1979 | Larsen |
| 4,984,302 | A | 1/1991 | Lincoln |
| 5,117,820 | A | 6/1992 | Robitaille |

(Continued)

FOREIGN PATENT DOCUMENTS

GB 392654 5/1933

(Continued)

OTHER PUBLICATIONS

"Turning Copper into Gold", *Red Herring*, Feb. 5, 2007, p. 23.

(Continued)

*Primary Examiner*—Steven O Douglas
*Assistant Examiner*—Rachel T Young
(74) *Attorney, Agent, or Firm*—Wolf, Greenfield & Sacks, P.C.

(57) ABSTRACT

A nasal comfort device provides humidified air to the nasal passages of a user. The device, which is attachable to a user's face, may include an evaporative surface and a reservoir that is fluidically connected to the evaporative surface. The reservoir may be positioned remotely from the evaporative surface and connected to the evaporative surface with a conduit. A support structure may include one or more support arms which maintain the evaporative surface below the nose. In some embodiments, the device may filter air instead of, or in addition to, humidifying the air. Medications or other agents may be included in the liquid being evaporated or on the evaporative surface.

37 Claims, 14 Drawing Sheets

U.S. PATENT DOCUMENTS

| | | | |
|---|---|---|---|
| 5,373,841 A | 12/1994 | Kyllonen et al. | |
| 5,392,773 A | 2/1995 | Bertrand | |
| 5,533,499 A | 7/1996 | Johnson | |
| 5,533,503 A | 7/1996 | Doubek et al. | |
| D379,513 S | 5/1997 | Ierulli | |
| 5,640,974 A | 6/1997 | Miller | |
| 5,706,800 A | 1/1998 | Cronk et al. | |
| D398,992 S | 9/1998 | Feret | |
| 5,890,486 A | 4/1999 | Mitra et al. | |
| 5,947,119 A | 9/1999 | Reznick | |
| D422,702 S | 4/2000 | Lundy et al. | |
| 6,116,236 A | 9/2000 | Wyss | |
| D441,081 S | 4/2001 | Mueller | |
| 6,276,360 B1 | 8/2001 | Cronk et al. | |
| 6,318,362 B1 | 11/2001 | Johnson | |
| 6,328,038 B1 | 12/2001 | Kessler et al. | |
| 6,354,293 B1 | 3/2002 | Madison | |
| 6,691,706 B2 * | 2/2004 | Ives | 128/204.13 |
| 6,701,924 B1 | 3/2004 | Land, Jr. et al. | |
| 6,769,428 B2 | 8/2004 | Cronk et al. | |
| 6,863,066 B2 | 3/2005 | Ogle | |
| 7,013,889 B2 | 3/2006 | Cronk et al. | |
| 2004/0118400 A1 | 6/2004 | Chou | |
| 2004/0166147 A1 | 8/2004 | Lundy et al. | |
| 2005/0235992 A1 | 10/2005 | Djupesland | |
| 2006/0112958 A1 | 6/2006 | Fisher et al. | |
| 2008/0092889 A1 * | 4/2008 | Tjia | 128/204.13 |

FOREIGN PATENT DOCUMENTS

| | | |
|---|---|---|
| GB | 583507 | 12/1946 |
| WO | WO 94/19043 A1 | 9/1994 |
| WO | WO 2004/004922 A1 | 1/2004 |
| WO | WO 2004/100828 A2 | 11/2004 |
| WO | WO 2006/023408 A2 | 3/2006 |

OTHER PUBLICATIONS

PCT Invitation to Pay Additional Fees and Partial Search Report for International Application No. PCT/US2007/003625, dated Aug. 7, 2007.

International Search Report and the Written Opinion of the International Searching Authority dated Nov. 8, 2007 from corresponding International Application No. PCT/US2007/003625.

* cited by examiner

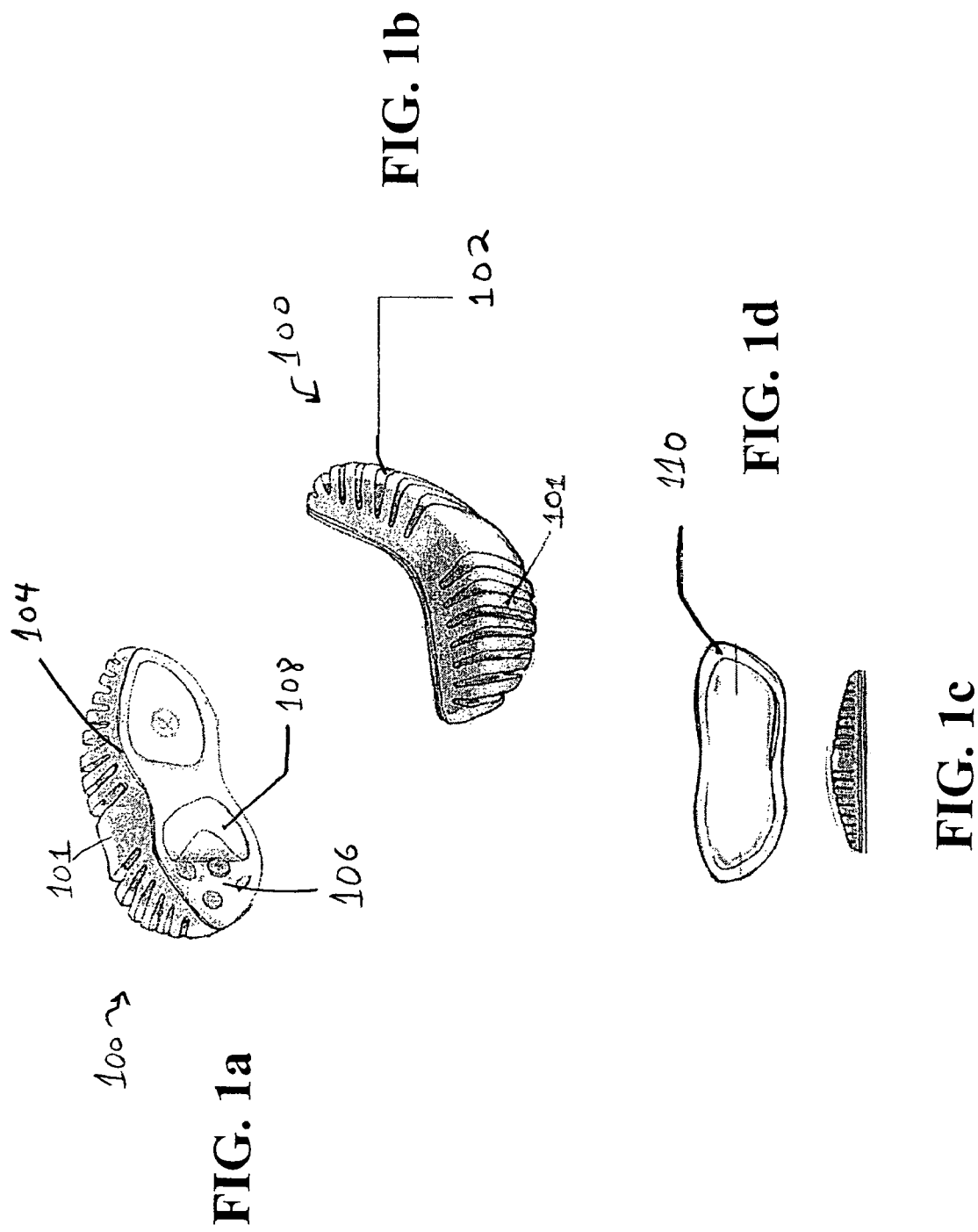

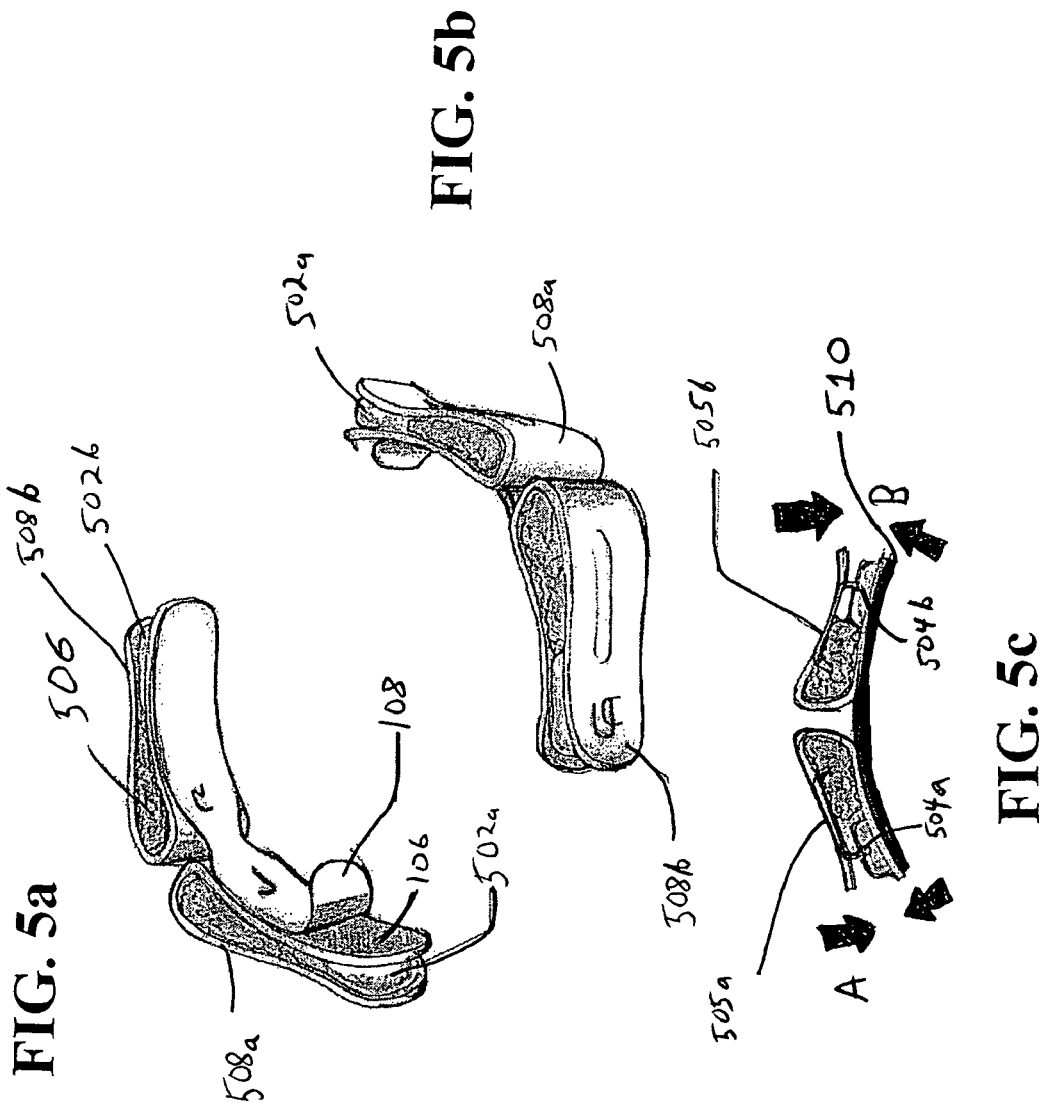

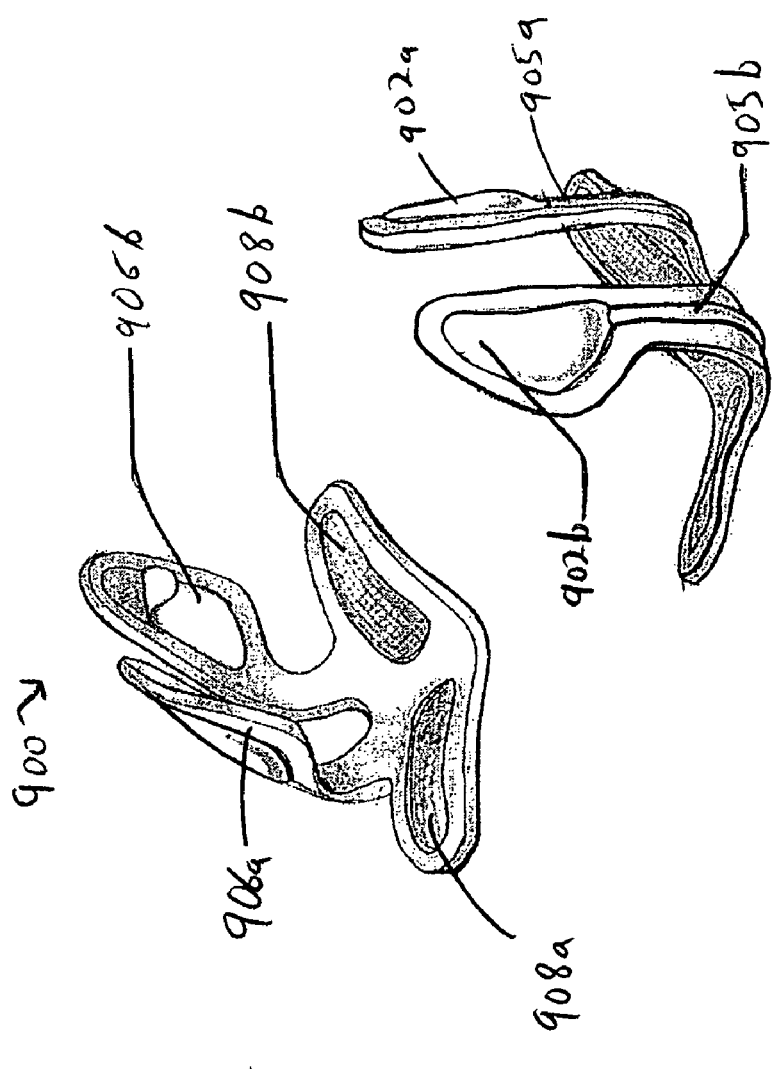

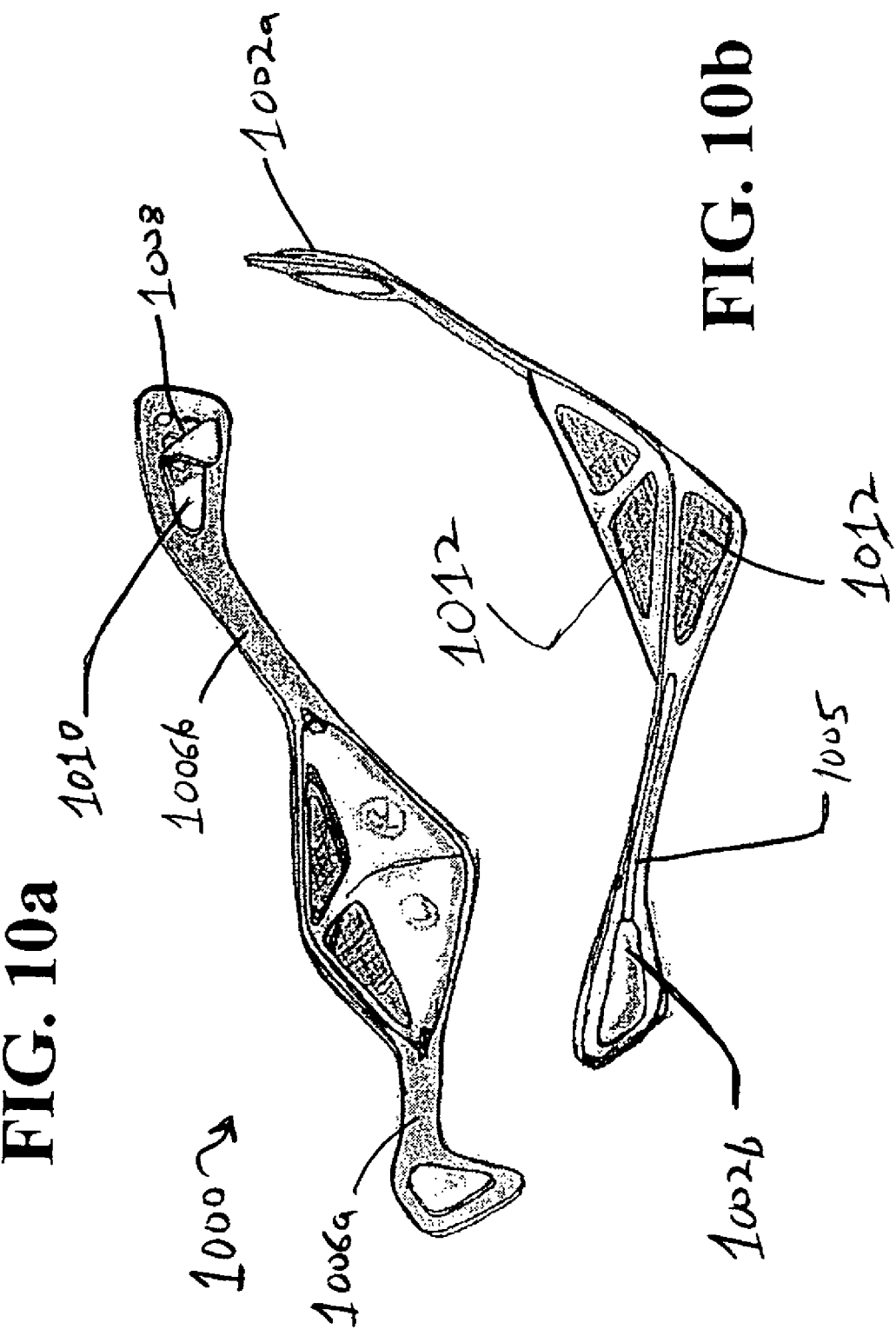

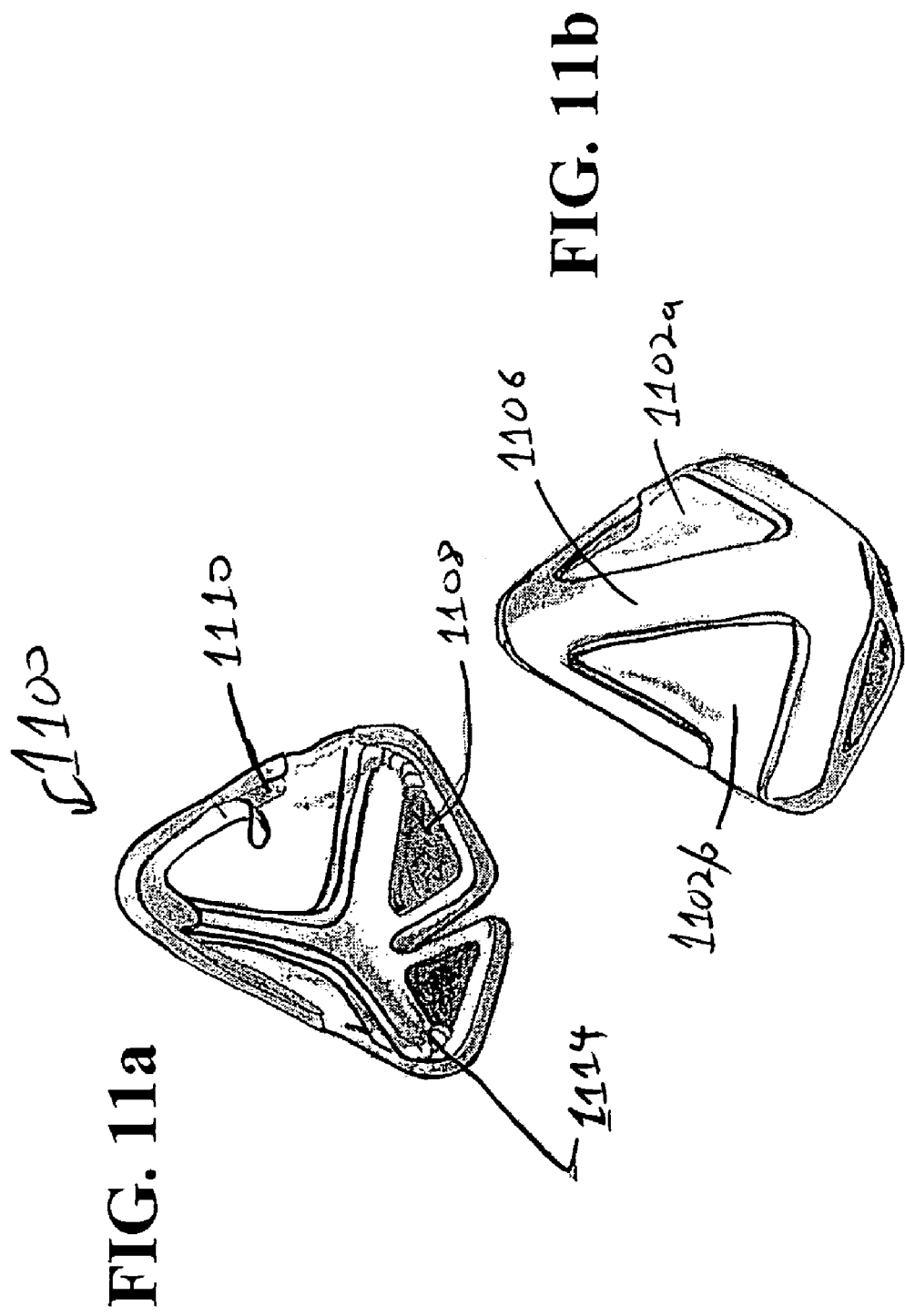

NASAL COMFORT DEVICES AND METHODS

RELATED APPLICATIONS

This application claims the benefit under 35 U.S.C. §119(e) to U.S. Provisional Application Ser. No. 60/771,800, entitled "Moisture Delivery Devices and Methods", filed on Feb. 9, 2006.

FIELD OF THE INVENTION

The invention relates generally to devices and methods for delivering moisture and/or other substances to the nasal passages, and more specifically to devices and methods which improve nasal comfort by evaporating liquid close the nose and/or by filtering air being drawn into the nose.

DISCUSSION OF THE RELATED ART

As part of the respiratory tract, nasal passages humidify and warm incoming air, and also filter particulates, bacteria, or other foreign materials as part of a first line of defense in protecting the body from these foreign materials. Dry air can adversely affect the ability of the nasal passages to provide these benefits, which can lead to significant comfort and/or health problems. Dry air is often an issue when traveling on an airplane, and areas with cold climates often have low humidity that is exacerbated by indoor heating.

Various nasal moisturizers are available in the form of nasal spray devices and bottles of nasal drops. These products typically include an aqueous solution of sodium chloride, a preservative, a buffer, and often a medication. In many cases, repeated application of the spray or drops is required to maintain moisturized nasal passages.

SUMMARY

Embodiments of the invention provided herein are directed to nasal comfort devices and methods which help to moisturize nasal passages and/or provide filtration of air being breathed in through the nose. According to one embodiment of the invention, a method of providing evaporated liquid to a user's nasal passage includes providing a device including a liquid-holding material, an evaporative surface and an attachment element. The method further includes adding liquid to the liquid-holding material, and, after adding liquid to the liquid-holding material, attaching the device to a user's face with the attachment element such that the evaporative surface is held below the user's nose and liquid moves from the liquid-holding material to the evaporative surface as liquid evaporates from the evaporative surface.

According to another embodiment of the invention, a packaged device for providing evaporated liquid to a user's nasal passages includes a device having a wetted liquid-holding material, an evaporative surface fluidically connected to the liquid-holding material, and an attachment element. The device is configured to be attached to a user's face such that the evaporative surface is held below the user's nose. A sealed package contains the device, and the sealed package is substantially impermeable to vapor of the liquid which is held by the liquid-holding material.

According to a further embodiment of the invention, a device for providing evaporated liquid to a user's nasal passage includes an evaporative surface configured to allow liquid to evaporate and an enclosed liquid reservoir constructed and arranged to provide a liquid to the evaporative surface. The device also includes an attachment element configured to maintain the evaporative surface in at least one of the following positions: a) in the nasal passage; b) at least partially covering a nostril; and c) below a nostril, such that evaporated liquid from the evaporative surface enters a nasal passage of the user.

According to another embodiment of the invention, a method of providing evaporated liquid to the nasal passages includes providing a device including an evaporative surface and a reservoir. The reservoir holds a liquid. The method further includes initiating evaporation by delivering the liquid from the reservoir to the evaporative surface, and also includes attaching the device to a user's face such that evaporated liquid from the evaporative surface enters the user's nasal passages.

According to another embodiment of the invention, a user-wearable device includes an air-permeable filter material and a support structure constructed and arranged to support the air-permeable filter material within a nasal passage and/or at least partially covering a nostril. The support structure comprises a first resilient support arm configured to adhere to skin on the user's face Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

DESCRIPTION OF FIGURES

FIG. 1a is a perspective rear view of a nasal comfort device according to one embodiment of the invention;

FIG. 1b is a perspective front view of the device illustrated in FIG. 1a;

FIG. 1c is a top view of the device illustrated in FIGS. 1a and 1b;

FIG. 1d is a front view of one embodiment of packaging for the device illustrated in FIGS. 1a-1c;

FIG. 2b is a perspective front view of the device illustrated in FIG. 2a;

FIG. 4b is a perspective front view of the device illustrated in FIG. 4a;

FIG. 5a is a perspective rear view of a device including a cover for the evaporative surface;

FIG. 5b is a perspective front view of the device illustrated in FIG. 5a;

FIG. 5c is a cross-sectional top view of the device illustrated in FIGS. 5a and 5b;

FIG. 6b is a view of one application of the device illustrated in FIG. 6a;

FIG. 7b is a view of one application of the device illustrated in FIG. 7a;

FIG. 9a is a perspective rear view of a nasal comfort device having support arms according to one embodiment of the invention;

FIG. 9b is a perspective front view of the device illustrated in FIG. 9a;

FIG. 10a is a perspective rear view of an alternative embodiment of the invention;

FIG. 10b is a perspective front view of the embodiment illustrated in FIG. 10a;

FIG. 11a is a perspective rear view of a further embodiment of the invention; and FIG. 11b is a perspective front view of the embodiment illustrated in FIG. 11a.

DETAILED DESCRIPTION

Figure 2A:
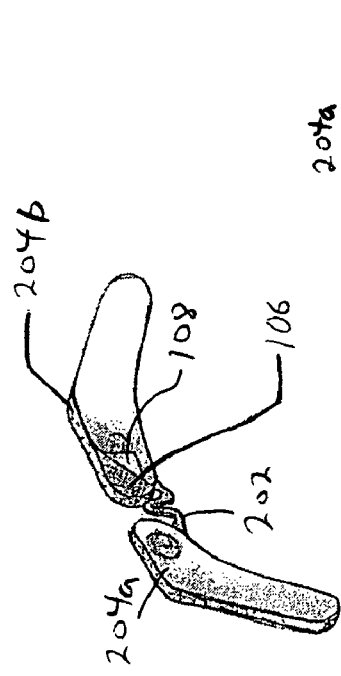
FIG. 2a is a perspective rear view of a nasal comfort device according to one embodiment of the invention.

For ease of understanding, and without limiting the scope of the invention, the nasal comfort devices to which this patent is addressed are disclosed below particularly in connection with devices that provide liquid evaporation and/or air filtration below a user's nose and above the user's upper lip. It should be appreciated, however, that the present invention can be used in other suitable locations.

The nasal comfort device includes an evaporative surface from which a liquid, such as water, may evaporate and enter the nasal passages of a user. The user may attach the evaporative surface to his or her face so that humidified air is continuously provided to the nasal passages as long as liquid is supplied to the evaporative surface. To facilitate continuous use, the device may be attachable to a user's face in any of a number of suitable manners. For example, the evaporative surface (e.g., a section of wetted open cell foam) may be adhered to a user's face above the upper lip and below the nose. In other examples, an elastic strap may be placed around the head or ears to hold an evaporative surface in place, or a clip may be configured to gently grasp the nasal septum. To maintain a supply of liquid for the evaporative surface, in some embodiments a liquid reservoir holding a volume of liquid is fluidically connected to the evaporative surface.

The liquid reservoir may be configured as a material with internal voids that is integral with or immediately adjacent to the evaporative surface. For example, a single volumetric piece of open cell foam provides both an evaporative surface and a liquid-holding capability which may act as a reservoir. In embodiments that include an integral reservoir and evaporative surface, as well as in other embodiments, capillary action may act to move the liquid from the reservoir to the evaporative surface.

To provide additional liquid capacity, the liquid reservoir may be configured as a separate, enclosed container that is connected via a conduit to the evaporative surface. In some embodiments a reservoir is remotely attachable to the user's face in a position where the reservoir is typically higher than the evaporative surface such that gravity helps to move the liquid to the evaporative surface. For example, a reservoir may be attached to a user's face in the vicinity of the cheekbone. In some embodiments a reservoir may be attached to a user's nose, and the support structure for the reservoir may double as a support arm for maintaining the position of the evaporative surface. In this manner, attachment to the face may be restricted to the nose only, resulting in a compact device that limits interference with normal activities. Capillary action or pressure-induced liquid movement may be used in embodiments where a remote reservoir is maintained below the evaporative surface. For longer term use, a high capacity reservoir may be held other than on the face, and any suitable manner of delivering the liquid to the evaporative surface may be employed.

Various materials may be used to provide an evaporative surface. In many cases, a material with a high surface area-to-volume ratio is desirable to reduce the size of the device while still providing suitable humidification of the air. In some embodiments specially designed evaporative structures may be used to increase the amount of surface area available for evaporation.

Supplying liquid to the reservoir and/or the evaporative surface may be achieved by pre-wetting one or both of the components before attaching the device to the user's face. In embodiments where the reservoir includes an absorbent liquid-holding material, water may be added to the reservoir by placing the material in water, for example, under a faucet. In some embodiments the device may be packaged in a pre-wetted configuration such that the device is ready for use immediately after opening the package.

Each device may be packaged separately and designed for a single use. In other embodiments, the device may include a refillable or replaceable reservoir. For embodiments which include reusable reservoirs that are designed to be placed in water, multiple adhesive strips may be provided on the device so that a new adhesive strip may be used for each new application of the device to the face.

Delivery of liquid from the reservoir to the evaporative surface may be activated in a simple manner according to various embodiments. For example, in some embodiments an adhesive strip may have a protective covering, and removal of the protective covering may open a valve or break a seal on the reservoir, thereby activating delivery of liquid. In some cases, the act of opening the packaging for the device may activate delivery of liquid. A breakable seal may be provided such that a piercing element or a peeling element creates an opening in the reservoir and allows flow of the enclosed liquid.

In addition to, or instead of, humidifying the air that enters a user's nasal passages, embodiments disclosed herein may provide a filtering facility. An air-permeable material may be positioned to partially or fully cover one or both nostrils such that air breathed in through the nose is filtered by the material. The material may be configured as a rudimentary check valve such that the material does not impede the flow of exhaled air. For example, the air-permeable material may have slits to allows sections of the material to separate when air is being exhaled. On the nasal passage side of the material, a highly permeable mesh material may provide a backing that prevents the slit material from separating when air is being inhaled.

In some embodiments the air-permeable material may be supplied with water or other liquid to humidify the air. In some embodiments separate materials are provided for filtering facility and the humidification facility.

As mentioned above, a single piece of material may be used as both a reservoir and an evaporative surface. One particular embodiment of a nasal comfort device is shown in FIGS. 1a-1c. In this embodiment, a device 100 is formed of an open cell foam material 101 including vertical slots 102.

A support base 104 consists of a flexible material which may be conformed to the skin of the user located between the nose and the upper lip. An adhesive backing 106 is provided on the backside of support base 104, and a protective cover 108 is provided to protect the adhesive strip until the device is ready for use. Layered adhesive backings (not shown) may be provided such that a new adhesive backing may be exposed for each use of the device. The device is attached below the user's nose, and as he breathes in through the nose, air traveling past and/or through the evaporative surface of the open cell foam 101 is humidified.

While support base 104 is shown as having an unbent free state in FIG. 1c, in some embodiments the device may be pre-formed to be in a curved configuration to reduce the tendency of the device to pull into a straight configuration when adhered to the user's face. In such embodiments, support base 104 still may be flexible for conformance to a user's face.

Slots 102 may be any suitable shape and be in any suitable configuration. For example, in some embodiments the slots are slanted and parallel, and in further embodiments each of the slots is oriented such that the top opening of the slot points toward the user's nostril. Depressions, patterns, and various other surface features may be used to provide evaporative surfaces with increased areas and/or help facilitate the flow of air over the evaporative surfaces en route to the nasal passages.

A foil package for the device is shown in FIG. 1d. In embodiments where the nasal comfort device is packaged in a pre-wetted state, the package may be hermetically sealed to prevent release of the moisture. In some embodiments the device may be sold in a dry state, and the user is instructed to add water to the absorbent material before attaching the device to the face. Of course, in some embodiments water may be added to the absorbent material after the device is attached to the user's face.

Figure 2B:
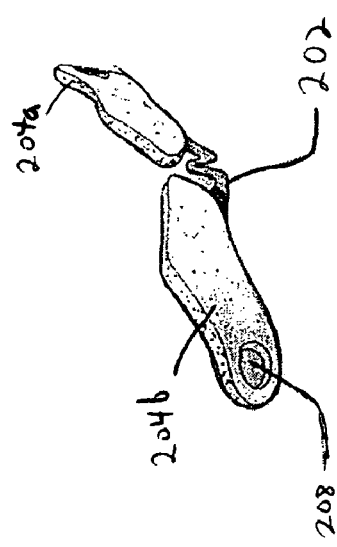

In another manner of providing conformance to a user's face, a nasal comfort device 200 including a flexible connector 202 is illustrated in FIGS. 2a-2b. Flexible connector 202 permits two pre-wetted foam pieces 204a and 204b to be adhered to the user's face at an angle to one another. Flexible connector 202 may be formed of a resilient material or a deformable material. In some embodiments, connector 202 may be configured to bend more easily in certain directions, for example, the connector may quite flexible in allowing horizontal pivoting of pieces 204a and 204b relative to one another, and be less flexible in allowing vertical pivoting of pieces 204a and 204b. Similar to the embodiment illustrated in FIGS. 1a-1c, a protective cover 108 may be provided over adhesive backing 106. An area 208 may be provided for logo placement. In an alternative embodiment, flexible connector 202 may include a gripping element that is placed in the nose to hold the device by gently grasping the nasal septum. Flexible connector 202 may be used with other embodiments described herein, including embodiments employing a remote reservoir.

An impervious barrier (not shown) may be provided along the downwardly-facing surface of foam pieces 204a, 204b to limit dripping and/or reduce evaporation in an area that does not provide as much humidification benefit as other areas. Such barriers may be used on other portions of the device and with other embodiments described herein.

Figure 3:
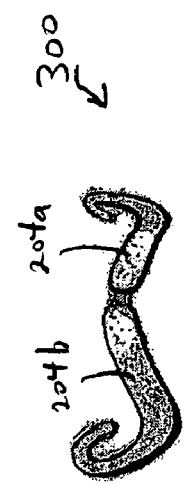
FIG. 3 is a perspective front view of an alternative embodiment of a device according to one embodiment of the invention.

The device may be configured in any suitable shape, including novelty shapes such as a moustache-shaped device 300, as shown in FIG. 3. The evaporative surface and/or reservoir may extend laterally beyond the sides of the nose. For purposes herein, a component is considered to be below the nose even if the component is not situated directly below the nose, but instead is positioned laterally lower than the bottom of the nose.

Figure 4A:
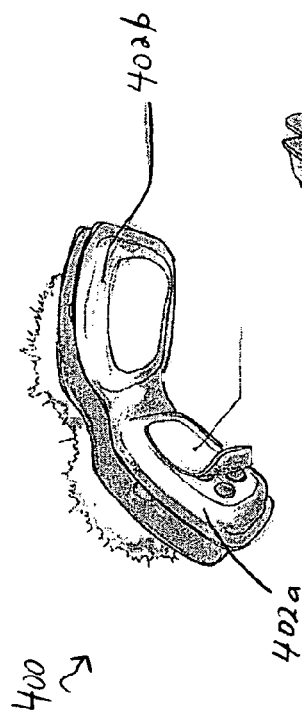
FIG. 4a is a perspective rear view of a device having an enclosed reservoir that is separate from the evaporative surface, according to one embodiment of the invention.
Figure 4B:
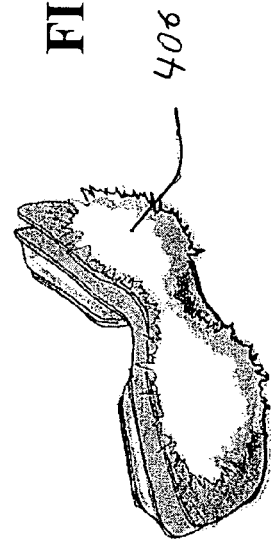
Figure 4C:
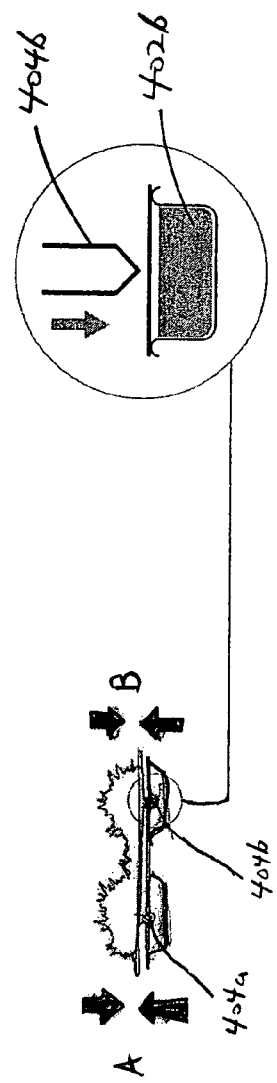
FIG. 4c is a cross-sectional top view of the device illustrated in FIGS. 4a and 4b.

One or more liquid containers may be provided to increase the liquid capacity of the device. One particular embodiment of a device 400 which includes containers as separate reservoirs is illustrated in FIGS. 4a-4c. In this embodiment two enclosed containers 402a and 402b containing liquid are positioned on the backside of device 400. Two piercing elements 404a and 404b are each configured to pierce a face of the containers when the front side and the backside of the device are squeezed toward each other, as represented by arrows A and B. Once the container has been pierced, the liquid drains directly into a material 406 that composes the evaporative surface. In the embodiment of FIGS. 4a-4c, the evaporative surface is a fibrous material having a large surface area and occupies a large volume. By providing an enclosed reservoir charged with liquid (e.g., water), evaporation from the evaporative surface may be initiated by delivering liquid from the reservoir to the evaporative surface. For purposes herein, "initiating evaporation" means starting the first substantial evaporation of liquid from the evaporative surface. For purposes herein, the term "charged" means filled or partially filled. Thus, a reservoir which is half-filled with liquid is considered to be charged with liquid.

As with other embodiments described herein, an adhesive backing 106 and protective cover 108 may be provided for attachment of the device to the user's face.

Another embodiment of a device that includes piercable containers is illustrated in FIGS. 5a-5c. In this embodiment, piercing elements 504a and 504b are part of capillary tubes 505a and 505b that provide conduits for liquid to travel from containers 502a and 502b to a material 506 which forms the evaporative surface. Squeezing the device, as represented by arrows A and B, pierces the containers, and capillary action draws the liquid from the containers 502a, 502b to the evaporative surface material 506.

For aesthetic purposes, covers 508a and 508b may be positioned to conceal portions of the evaporative material and/or the containers. The covers are shown in this embodiment as extending along the front side of the device and continuing to the backside of the evaporative surface material. The portions of the covers which extend to the backside are secured to a support base 510. In other embodiments the covers may be present only along the front of the evaporative surface material and/or the containers.

In addition to aesthetic purposes, covers 508a, 508b, depending on the material used, may limit evaporation from the covered surfaces. This limitation on evaporation may extend the useful life of the device by restricting evaporation to an area where humidification is most useful. Of course, in some embodiments vapor permeable material may be used for covers 508a, 508b to permit evaporation even in the covered areas.

As with other embodiments, an adhesive backing 106 and a protective cover 108 may be included for attachment of the device to the user's face.

Figure 6A:
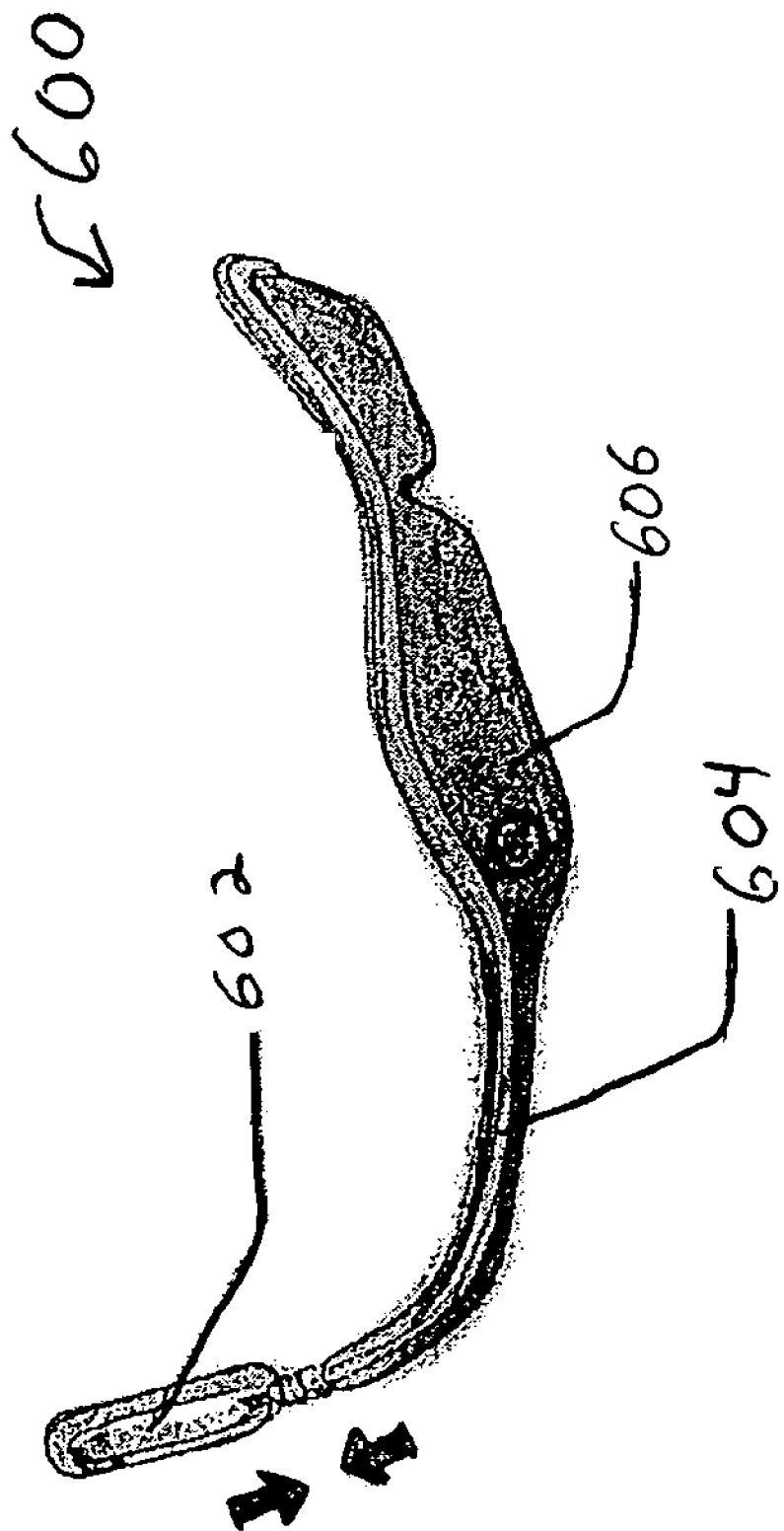
FIG. 6a is a perspective front view of a nasal comfort device including a reservoir that is remote from the evaporative surface.
Figure 6B:
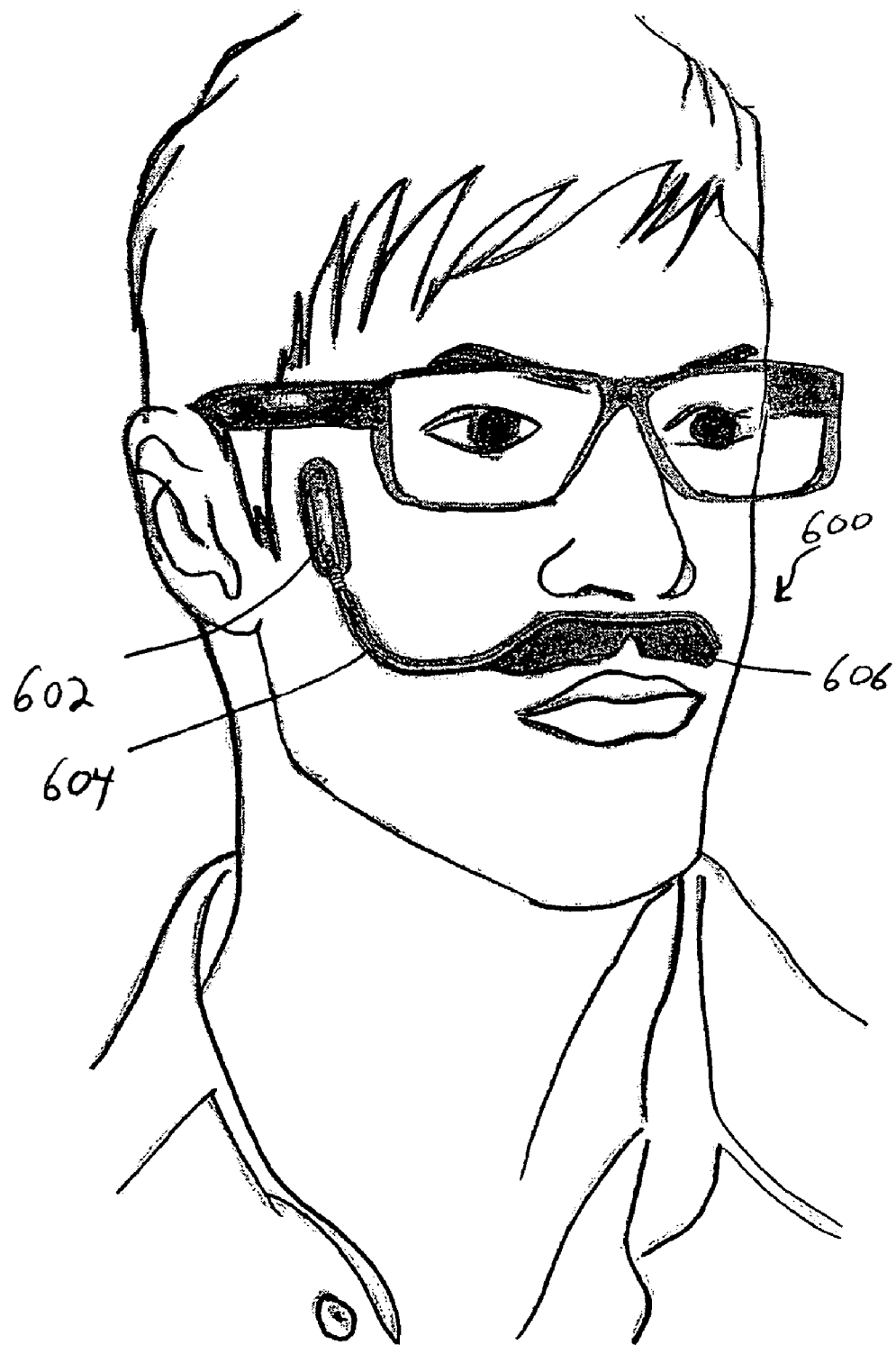

FIGS. 6a and 6b show a device 600 which includes a remote reservoir 602 that is fluidically connected to an evaporative surface by a conduit 604. In this particular embodiment, delivery of liquid from the reservoir to the evaporative surface may be initiated by pushing an end of conduit 604 into reservoir 602 to puncture a seal and connect the conduit to reservoir 602. By positioning reservoir 602 on the user's face above the evaporative surface (see FIG. 6b), gravity may help to deliver liquid through conduit 604. A brushed polyester fabric 606, such as Coolmax® available from DuPont, is used in this embodiment to form the evaporative surface, although any suitable material may be used.

Figure 7A:
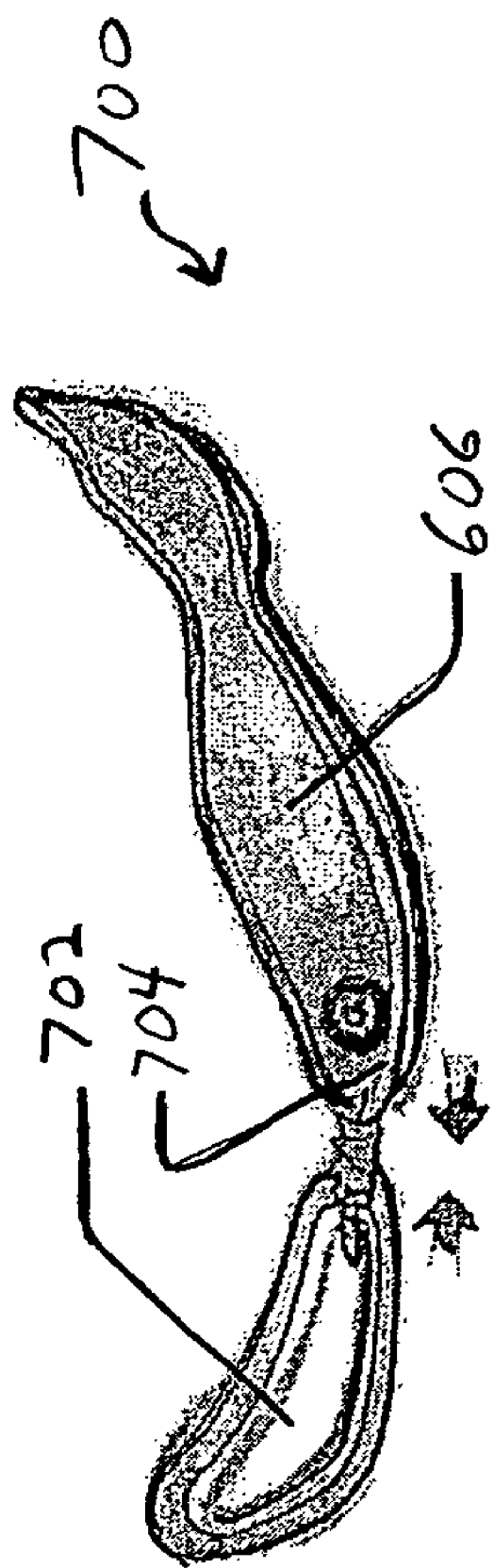
FIG. 7a is a perspective front view of a device configured to move liquid primarily via capillary action, according to one embodiment of the invention.
Figure 7B:
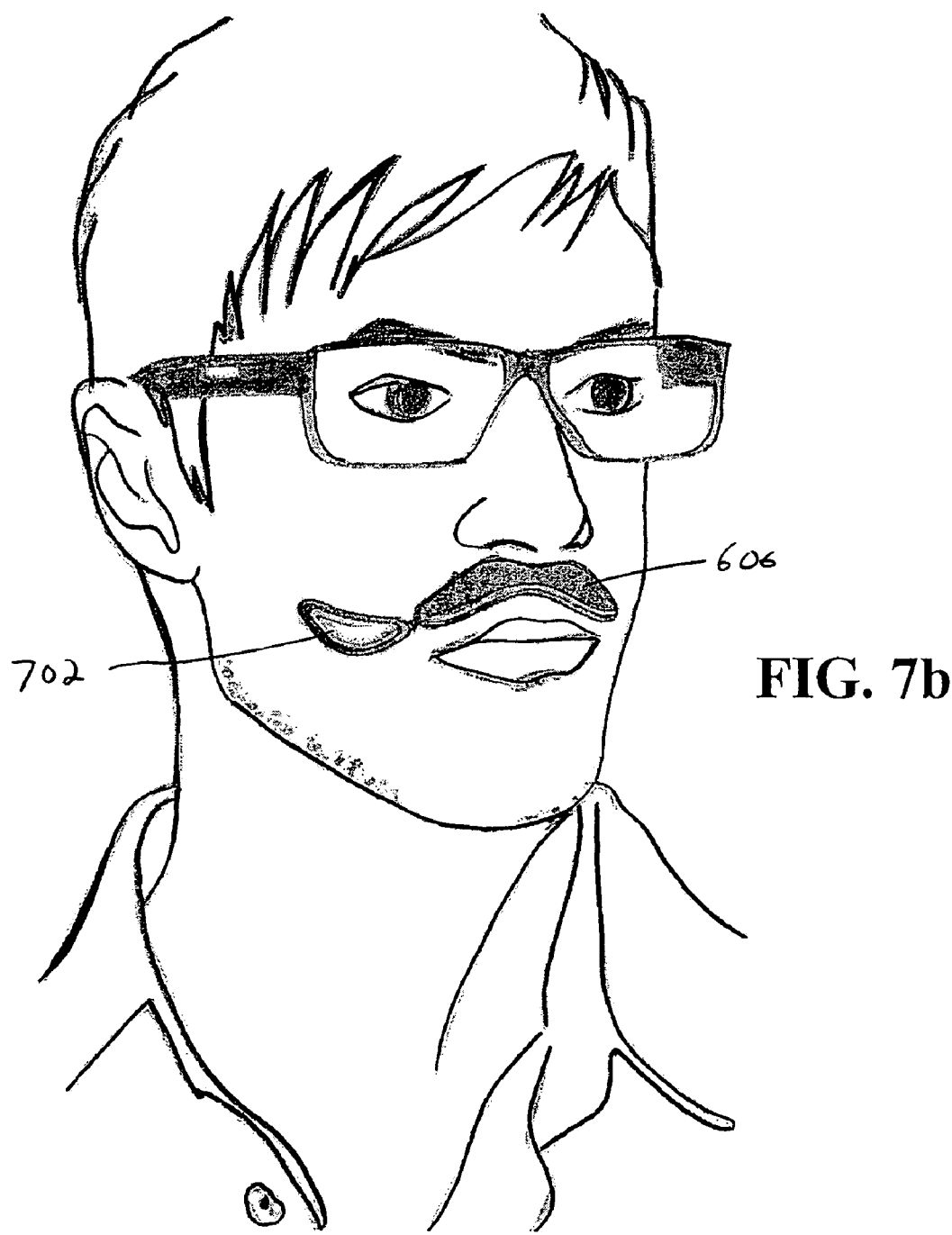

Another embodiment employing a remote reservoir is illustrated in FIGS. 7a and 7b. In this embodiment, a nasal comfort device 700 includes a reservoir 702 that is configured to be positioned below a substantial portion of an evaporative surface. In this embodiment, capillary action is the primary force that delivers liquid to the evaporative surface. To initiate flow of the liquid, a capillary tube 704 is pushed into reservoir 702, although any suitable method of initiating flow may be used. In some embodiments reservoir 702 may be removable and refillable so that device 700 can be re-used. In other embodiments, for example embodiments where the liquid includes a medication or other agent, reservoir 702 may be considered to be a single use component, and when spent, reservoir 702 may be replaced with a new, fully charged reservoir.

As with the device illustrated in FIG. 6a, the evaporative surface of device 700 may be formed with a brushed polyester fabric, although any suitable material may be used, including materials other than fabrics, such as a porous stone or other inflexible material.

FIGS. 6a and 7a are but two examples of the many contemplated embodiments of a nasal comfort device having remote reservoirs according to the present invention. While the reservoirs of these two embodiments are shown on one side of the device only, a second reservoir may be positioned on the opposite side of the device and/or additional reservoirs (remote or adjacent to the evaporative surface) may be included.

Figure 8:
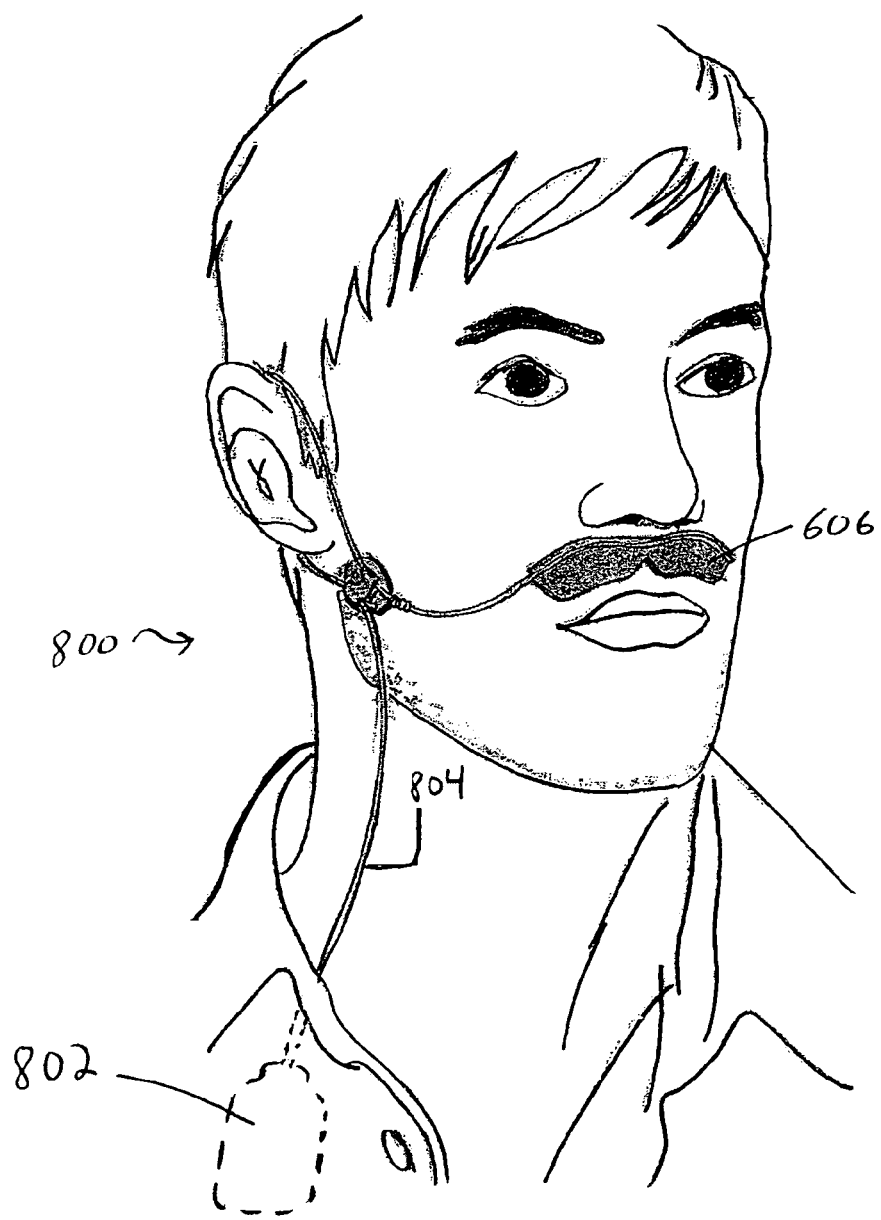
FIG. 8 is a view of one embodiment of a nasal comfort device including a concealed reservoir.

For longer term use, a high capacity reservoir may be used and held at a location other than on a user's face. For example, as shown in FIG. 8, a device 800 may include a high capacity reservoir 802 which may be placed or held somewhere other than the user's face. For example, high capacity reservoir 802 may be concealed within the user's clothing, and tubing 804 may be looped around the user's ear to maintain tubing 804 in a convenient position. A small pump (not shown) or a compressed air source (not shown) may be used to deliver liquid from the reservoir through tubing 804. In some embodiments the user may periodically squeeze reservoir 802 to deliver liquid to the evaporative surface 606.

High capacity reservoir 802 may be suspended above the evaporative surface in certain applications, such as when the user is a patient in a bed and reservoir 802 is suspended on an IV stand. An adjustable valve may be included to permit control of the rate of delivering liquid to evaporative surface 606. In some embodiments liquid may automatically be delivered intermittently to the evaporative surface. For example, a small pump may be controlled to periodically activate for set time period.

Figure 9C:
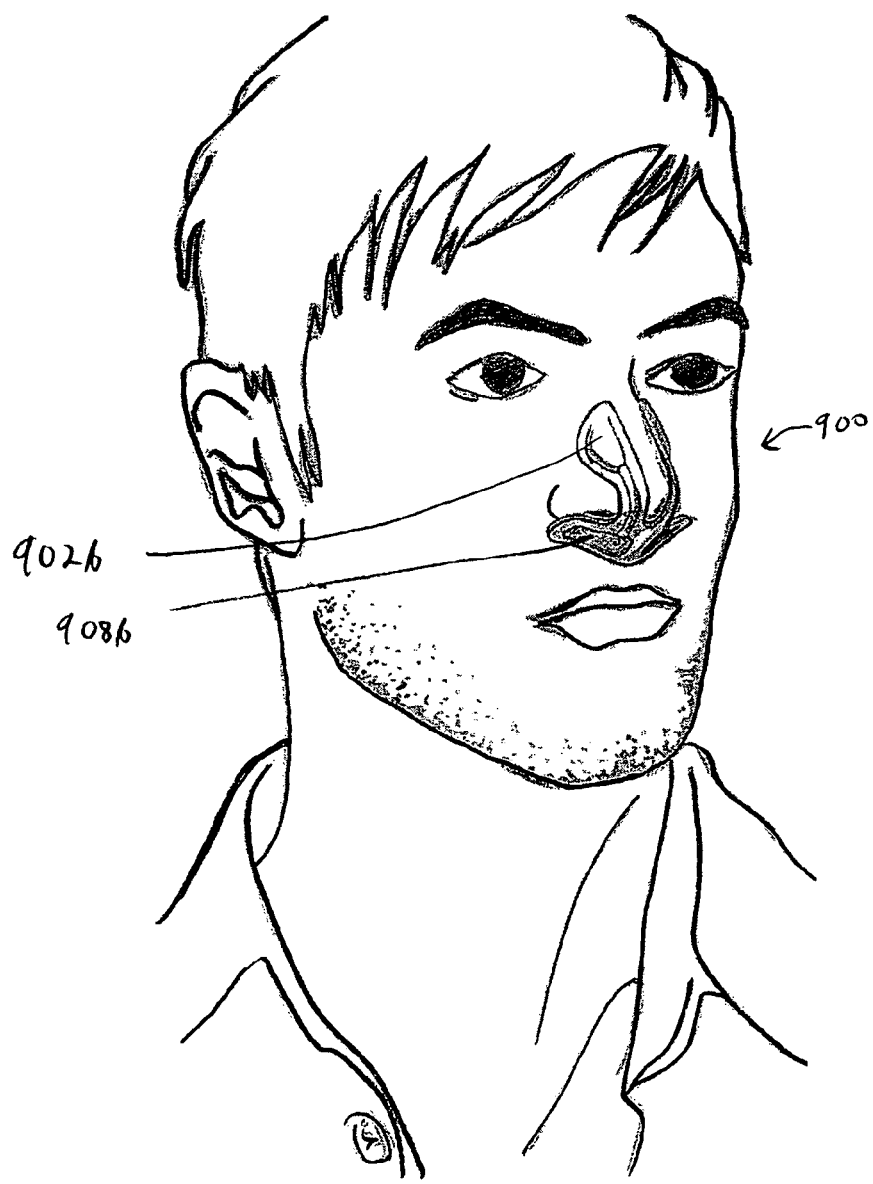
FIG. 9c is a view of one application of the device illustrated in FIGS. 9a and 9b.

The evaporative surfaces do not necessarily need to be supported by attaching the device to the skin under the user's nose. As shown in FIGS. 9a-9c, one or more support arms may be attached to a user's nose to maintain the evaporative material below the user's nostrils and/or at least partially externally covering the user's nostrils. In this particular embodiment, a device 900 includes a first support arm 906a and a second support arm 906b, each of which is adhered to opposite sides of the user's nose. In other embodiments, only one support arm or three or more support arms may be used as part of the support structure. The evaporative surface may include two separate pieces of material 908a and 908b, or may include a single piece of material that spans both nostrils. In this particular embodiment, support arms 906a, 906b do not connect to one another across the bridge of the user's nose. Instead, each of the support arms is connected to the somewhat horizontal portion of the device which secures the material pieces 908a, 908b. In still further embodiments, two separate devices, each with one support arm and configured to address one nostril, may be used together without a physical connection between the two.

Reservoirs 902a and 902b may be incorporated into support arms 906a, 906b and fluidically connected to the evaporative surfaces with tubes 905a and 905b. Initiation of flow from the reservoirs may be accomplished by opening a valve (not shown) or breaking a seal between the reservoir and the tubes. In other embodiments, a breakable seal may be provided within the tubes or at the end of the tubes near to the evaporative surfaces.

In addition to providing humidification of incoming air, device 900 may be constructed and arranged to filter the air as well. In some embodiments material pieces 908a and 908b may be air-permeable and positioned such that they cover or at least partially cover the user's nostrils. In some embodiments a nasal comfort device may be used only to filter air and not necessarily to provide moisture to the nasal passages. Activated carbon or other substances may be used as part of a filter material. Separate materials may be used to provide the humidification and filtering facilities in a single device.

Figure 10C:
FIG. 10c is a view of one application of the embodiment illustrated in FIGS. 10a and 10b.

For embodiments employing one or more support arms, the support arms may be attached to the user's face at locations other than the nose. For example, as shown in FIGS. 10a-10c, a device 1000 includes support arms 1006a and 1006b which extend outwardly and upwardly from below the user's nose and attach to the face to the sides of the user's nose. Each arm 1006a, 1006b includes an adhesive backing 1008 and a protective cover 1010. It will be appreciated by those of skill in the art that the support arms may be attached in other suitable locations, and adhesive backing may be included on the portion of the device below the user's nose as supplemental support. Reservoirs 1002a and 1002b may be provided near the attachment areas of device 1000 and may be fluidically connected to an evaporative surface and/or filter material 1012 with conduits 1005a and 1005b. Of course, in some embodiments no remote reservoirs are provided.

Instead of including a layer of material as shown in the embodiment of FIGS. 9a-9c, the evaporative surface and/or filter material 1012 may enclose a volume such that additional material may be held below the nose. Examples of materials that may be held within the volume include activated charcoal, agents intended to neutralize pollutants or poisons, medications, and materials with large surface areas for evaporation.

For sturdy support and high liquid capacity, which may be useful attributes when using a nasal comfort device while sleeping, in some embodiments a device may cover substantial portions of the nose and/or extend along a substantial perimeter of the nose. For example, as shown in the embodiment of FIGS. 11a-11b, a device 1100 is constructed and arranged to cover a user's nostrils and substantially encompass the entire nose. Here, a support arm 1106 extends vertically along the bridge of the nose and branches to either side of the nose at the top. Large reservoirs 1102a and 1102b are provided within areas not occupied by the support arm and evaporative surface material 1108. In this manner, a substantial portion of the nose is covered, but not the mouth. An adhesive backing 1110 may be provided along various portions of support arm 1106. Frangible tubing 1114 may be provided between each reservoir and its associated evaporative surface material to function as a single use valve to initiate flow of liquid to the evaporative surfaces.

To kill bacteria, fungi and viruses, substances may be incorporated into components of the various embodiments described herein. In some embodiments, fabrics may be used which include fibers having incorporated copper oxide.

The order of acts of the methods described and claimed herein do not necessarily need to be performed in the order listed unless an order to the acts is distinctly recited.

Having thus described several aspects of several embodiments of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A device for providing evaporated liquid to a user's nasal passage comprising:
    an evaporative surface configured to allow liquid to evaporate;
    an enclosed liquid reservoir constructed and arranged to provide a liquid to the evaporative surface;
    an attachment element configured to maintain the evaporative surface in at least one of the following positions by adhering the device to a user's skin: a) in a user's nasal passage; b) at least partially covering a user's nostril; and c) below a user's nostril, such that evaporated liquid from the evaporative surface enters the user's nasal passage;
    an adhesive element; and
    a protective covering that covers the adhesive element; wherein
    the protective covering is constructed and arranged such that removal of the protective covering from the adhesive element initiates a movement of liquid from the liquid reservoir to the evaporative surface.

2. A device as in claim 1, wherein the liquid reservoir is charged with water.

3. A device as in claim 1, wherein the liquid reservoir is charged with a liquid comprising medication.

4. A device as in claim 1, wherein the liquid reservoir is charged with a liquid comprising a neutralizing agent.

5. A device as in claim 1, wherein the liquid reservoir is configured to be maintained at a location on the user remote from the evaporative surface, and the liquid reservoir is fluidically connected to the evaporative surface with a conduit.

6. A device as in claim 5, further comprising an adhesive element on the reservoir which is configured to attach the reservoir to a user's face.

7. A device as in claim 1, wherein the device is configured to provide the liquid from the liquid reservoir to the evaporative surface via capillary action.

8. A device as in claim 1, wherein the device is configured to provide the liquid from the liquid reservoir to the evaporative surface using gravity.

9. A device as in claim 1, wherein the adhesive element is positioned on the device such that adhering the adhesive element above a user's upper lip and below a user's nose maintains the evaporative surface in at least one of positions a, b and c.

10. A device as in claim 1, wherein the attachment element is configured to maintain the evaporative surface in position b.

11. A device as in claim 1, wherein the attachment element is configured to maintain the evaporative surface in position c.

12. A device as in claim 1, wherein the reservoir comprises a sealed container charged with a liquid, the container having a breakable seal.

13. A device as in claim 12, wherein
    the protective covering and the breakable seal are constructed and arranged such that removal of the protective covering from the adhesive strip breaks the breakable seal.

14. A device as in claim 12, further comprising a piercing element configured to break the breakable seal.

15. A device as in claim 1, further comprising a valve that is changeable from a first state in which the valve prevents movement of liquid between the liquid reservoir and the evaporative surface to a second state in which the valve permits movement of liquid between the liquid reservoir and the evaporative surface.

16. A device as in claim 1, wherein the evaporative surface comprises an open cell foam.

17. A device as in claim 1, wherein the evaporative surface comprises a brushed polyester material.

18. A device as in claim 1, further comprising a cover that is positioned to conceal a portion of the evaporative surface.

19. A device as in claim 1, wherein the attachment element comprises a first resilient support arm configured to adhere to skin on the exterior of a user's nose.

20. A device as in claim 19, wherein the first resilient support arm includes the enclosed liquid reservoir.

21. A device as in claim 1, wherein the liquid reservoir is removable from the device.

22. A device as in claim 21, further comprising a replacement liquid reservoir that can replace the liquid reservoir.

23. A device as in claim 1, wherein at least one component of the device comprises copper oxide.

24. A device as in claim 1, wherein a neutralizing agent is present on the evaporative surface.

25. A method of providing evaporated liquid to nasal passages, the method comprising:
    providing a device including an evaporative surface and a reservoir, the reservoir holding a liquid, the device further including an attachment element, an adhesive element and a protective covering that covers the adhesive element;
    initiating evaporation by delivering the liquid from the reservoir to the evaporative surface, wherein delivering the liquid from the reservoir to the evaporative surface includes initiating movement of the liquid from the liquid reservoir to the evaporative surface by removing the protective covering; and
    adhering the device to skin on a user's face such that evaporated liquid from the evaporative surface enters a user's nasal passages.

26. A method as in claim 25, wherein delivering the liquid from the reservoir to the evaporative surface comprises opening a valve to allow delivery of the liquid to the evaporative surface.

27. A method as in claim 25, wherein the reservoir comprises a sealed container and delivering the liquid from the reservoir to the evaporative surface comprises opening the container to allow delivery of the liquid to the evaporative surface.

28. A method as in claim 25, wherein delivering the liquid from the reservoir to the evaporative surface comprises delivering the liquid from the reservoir to the evaporative surface via a conduit.

29. A method as in claim 25, wherein delivering the liquid from the reservoir to the evaporative surface comprises positioning the reservoir and the evaporative surface such that gravity provides a force for delivering the liquid to the evaporative surface.

30. A method as in claim 25, wherein delivering the liquid from the reservoir to the evaporative surface comprises delivering the liquid from the reservoir to the evaporative surface via capillary action.

31. A method as in claim 25, wherein the act of attaching the device to a user's face is performed before the act of initiating evaporation.

32. A method as in claim 25, wherein the act of attaching the device to a user's face comprises positioning the evaporative surface below the user's nose.

33. A method as in claim 32, wherein the act of attaching the device to a user's face comprises positioning the evaporative surface above a user's upper lip.

34. A device as in claim 19, wherein the first support arm is configured to adhere to skin on a first side of the exterior of the user's nose, and further comprising a second resilient support arm that is configured to adhere to a second side of the user's nose, the second side being on the opposite side of a bridge of the nose from the first side.

35. A device as in claim 34, wherein the first resilient support arm includes the enclosed liquid reservoir.

36. A device as in claim 35, wherein the second resilient support arm includes a second enclosed liquid reservoir.

37. A device as in claim 1, wherein the attachment element comprises an adhesive element configured to adhere to a user's skin, wherein the adhesive element that is covered by the protective coating includes the adhesive element that is configured to adhere to the user's skin.

* * * * *